United States Patent
Mucciardi et al.

(10) Patent No.: US 6,474,164 B1
(45) Date of Patent: Nov. 5, 2002

(54) NOISE SUPPRESSION AND SIGNAL ENHANCEMENT SYSTEM FOR ULTRASONIC NON-DESTRUCTIVE INSPECTION/EVALUATION

(75) Inventors: Anthony N. Mucciardi, Silver Spring, MD (US); Thomas J. Tilden, Warrenton, VA (US)

(73) Assignee: SLX, Inc., Silver Spring, MD (US)

( * ) Notice: Subject to any disclaimer, the term of this patent is extended or adjusted under 35 U.S.C. 154(b) by 136 days.

(21) Appl. No.: 09/638,400

(22) Filed: Aug. 15, 2000

Related U.S. Application Data (60) Provisional application No. 60/149,695, filed on Aug. 20, 1999.

(51) Int. Cl.[7] ............................................. G01N 29/00
(52) U.S. Cl. ............................ 73/602; 73/626; 73/628
(58) Field of Search ........................ 73/602, 625, 626, 73/628; 600/442, 447, 448; 367/901; 702/191, 280

(56) References Cited

U.S. PATENT DOCUMENTS

| | | | |
|---|---|---|---|
| 3,604,250 A | | 9/1971 | Grandia .................... 73/609 |
| 4,015,464 A | * | 4/1977 | Miller et al. ................ 73/61 R |
| 4,539,525 A | * | 9/1985 | Brown ....................... 330/107 |
| 5,050,226 A | | 9/1991 | Collet-Billon .............. 382/261 |
| 5,396,285 A | | 3/1995 | Hedberg et al. ............. 600/448 |
| 5,471,878 A | | 12/1995 | Chiao et al. .................. 73/602 |
| 5,487,389 A | * | 1/1996 | Benjamin et al. ......... 73/861.25 |
| 5,513,531 A | | 5/1996 | Sapia et al. ................... 73/602 |
| 5,671,154 A | | 9/1997 | Iizuka et al. .................. 702/39 |
| 5,804,728 A | | 9/1998 | Beall et al. ................... 73/598 |
| 5,882,307 A | * | 3/1999 | Wright et al. ............... 600/442 |
| 6,055,861 A | * | 5/2000 | Banta, Jr. et al. ............. 73/626 |
| 6,120,446 A | * | 9/2000 | Ji et al. ....................... 600/437 |
| 6,223,599 B1 | * | 5/2001 | Langdon et al. .............. 73/627 |
| 6,358,205 B1 | * | 3/2002 | Ustuner et al. ............. 600/437 |

* cited by examiner

*Primary Examiner*—Daniel S. Larkin
*Assistant Examiner*—Jacques Saint-Surin
(74) *Attorney, Agent, or Firm*—James Creighton Wray; Meera P. Narasimhan (57) ABSTRACT

The Noise Suppressor II provides procedures and add-on units, which are attached to standard analog or digital ultrasonic flaw detector instruments for either suppressing noise spikes that clutter the flaw detector screens, or other undesired signals, or enhancing weak, barely detectable signals. The add-on units may do both simultaneously as well. Each unit includes an adjustable filter so that a user may tune the filter bandwidth to a specific range within the overall transducer band that coincides with the signal to be either suppressed or enhanced.

31 Claims, 7 Drawing Sheets

FIG. 8A
Noise Suppression

Before

FIG. 8B
Noise Suppression

After

FIG. 8C
Signal Enhancement

Before

FIG. 8D
Signal Enhancement

After

NOISE SUPPRESSION AND SIGNAL ENHANCEMENT SYSTEM FOR ULTRASONIC NON-DESTRUCTIVE INSPECTION/EVALUATION

This application claims the benefit of 60/149,695, filed Aug. 20, 1999.

SUMMARY OF THE INVENTION

Add-on units are attached to standard analog or digital ultrasonic flaw detector instruments for either suppressing noise spikes that clutter up the flaw detectors' screens or enhancing very weak, barely detectable signals. The add-on units may do both simultaneously as well. Each unit includes an adjustable filter so that a user may tune the filter bandwidth to a specific range within the overall transducer band that coincides with the signal to be either suppressed or enhanced.

Each adjustable filter may use a variable filter circuit. The filter has independent controls for frequency, bandwidth and null/gain adjustments. The unit also includes a pre-amplifier for boosting weak signals prior to filtering. The unit may be added to any ultrasonic non-destructive inspection/evaluation (UT NDI/E) equipment and operates independently of that equipment. The unit operates in any of the three UT NDI/E inspection modes: pulse-echo, pitch-catch and through-transmission. The unit operates on single signals and in real-time. The unit has a small enclosure so that it may be portable and operated by a battery or an ac adapter.

The new Noise Suppressor II (NSII) system combines three independent functions, two tunable filters and one pre-amplifier, into one unit that provides a means for either suppressing noise signals (spikes or background noise) or enhancing a signal of interest by increasing the signal/noise ratio, or both.

The system is used as an add-on module to ultrasonic pulser/receiver instruments. These instruments may be either analog or digital devices that are components in an overall ultrasonic (UT) non-destructive inspection/evaluation (NDI/E) system, or they may be stand-alone self-contained UT instruments, usually called flaw detectors, that are commonly used in either manual, semi-automated or fully automated UT NDI/E applications. Even though these UT instruments may have some built-in noise suppression and/or signal enhancement capabilities, these are usually fairly rudimentary and hard-wired such that the user has no choices other than those supplied by the instrument manufacturer. As an add-on module, the NSII system's purpose is to enhance the function of the UT instrument by giving the user a set of signal filtering controls that are tunable to the particular needs of each application. As such, the NSII provides a significant increase in noise suppression and/or signal enhancement capabilities, all under user control.

The primary purpose of the NSII is to enhance signals returned from UT transducers being used as part of the NDI/E process. One of the main problems associated with UT flaw detector instruments is discriminating the response (either pulse-echo, pitch-catch or through-transmission) of a flaw from the background noise. Flaw detectors operate normally in a very wide band mode, whereas the signal returned from the transducer is much narrower in bandwidth. A simple narrow band filter may be used to substantially lower the noise floor and to enhance the signal/noise ratio.

One of the problems, however, is that the returned echo is not always centered on the same frequency as the built-in bandpass filter. The signal returned from the transducer is typically fairly wide band and different types of defects (i.e. targets) are represented in different bands of the incident signal. Also, UT transducers themselves may resonate at different frequencies and this varies with the type of transducer being used.

It is therefore highly desirable that the filter be tunable (i.e., adjustable) so that the user may "tune" the filter band to the specific range within the overall transducer band that coincides with the signal to be either suppressed or enhanced. This is similar to tuning a stereo receiver to find the optimal frequency position that delivers the best signal for a broadcasting station of interest. The NSII provides three functions that permit the user to tune either of the two filters' bands: (1) center frequency of at least 0.5 MHz (preferably ranges between 0.5 to 1.3 MHz and between 1.5 MHz to 7 MHz), (2) width of the band (narrow, medium, wide), and (3) amplification, either positive or negative, in the band (Gain=+15 dB or Null=−20 dB). Frequency ranges of about 0.15 to about 25 MHz are provided by embodiments of the invention.

Noise suppression is desirable when the noisy signal(s) is(are) induced by the material or the flaw detector itself. Noise from external sources (i.e., environmental noise) can also present problems due to their superposition on the small return responses from defects and the subsequent need for high amplification in the UT instrument to detect these small signals. External noise can sometimes literally mask the signal of interest or at least make its detection very difficult. Examples of high-amplitude external noise sources include electrical noise from positioning motors of a scanning system and welding machines.

It is therefore desirable that the filter be able to remove certain frequency bands as well as enhance the main frequency. It is also necessary to vary the bandwidth of the filter to match the bandwidth of the desired signal or noise source to obtain optimal signal enhancement.

The NSII does all of these things over a frequency range compatible with most ultrasonic NDI/E testing: at least 0.5 MHz with preferred ranges of about 0.5 to 1.3 MHz and 1.5 MHz to 7 MHz, or about 0.15 to about 25 MHz. The effectiveness of the NSII is increased by including two filter elements that permit combinations of noise suppression, signal enhancement or both. In theory, more stages may be added until the filters start interfering with one another due to bandwidth considerations.

The NSII contains a pre-amplifier as a third independent function. The preamp is adjustable by the user over a 0 dB to 30 dB range, in steps of 10 dB. The preamp's purpose is to boost weak signals (up to 30 dB) prior to any filtering operation(s) or to act as a stand alone additional amplification boost when no filtering is desired. This latter condition is commonly encountered when running long cable lengths between the UT transducer and its receiving UT instrument. The total gain of the system, therefore, is equal to 60 dB which derives from +30 dB in the preamp and +15 dB in each of the two filters if both filters are being used for signal enhancement.

The preferred Noise Suppressor II™ is an add-on unit to ultrasonic pulser/receivers and flaw detectors. The unit can be set to either suppress noise (spikes or background) or to enhance the signal/noise ratio of weak desirable signals, or both.

The preferred Noise Suppressor II™ combines three independent functions that can be used in any combination—preamp (up to 30 dB in 10 dB steps) and two tunable bandpass filters. The unit incorporates novel circuitry that enables the inspector to tune each filter anywhere in the 1.5–7.0 MHz band, the ultrasonic band most commonly used for inspection. The width of the band is also adjustable (low, mid, high) and each filter can either be set to null out a noise signal (−20 dB attenuation applied in the tuned band) or to enhance a desired signal (+15 dB gain applied in the tuned band). One filter can be used to null noise while the other is set to simultaneously enhance a desired signal, or both filters can be set identically to effectively "double up" on either noise cancellation (via −40 dB total attenuation) or signal enhancement (via +30 dB total gain).

The NSII is connected between the transducer(s) and the pulser/receiver or flaw detector. It is housed in a small (4"×7"×1.5") enclosure weighing less than two pounds and is powered by either a 9 v battery or AC. It operates in both pulse-echo or pitch-catch/thru-transmission modes. All settings are via detented rotary dials so that the user is assured of repeatable inspections. The unit interfaces with any type of analog or digital ultrasonic unit to provide an add-on enhancement.

The Noise Suppressor II (NSII) combines both PreAmp and Dual Channel Tunable Filter functions. Either function can be used alone or combined. Each of the two filters is tunable in both frequency and bandwidth, and each can either boost (bandpass filter) or cut (notch filter) the signal. The dual filters operate independently and can be tuned simultaneously to different frequencies, for instance 2.25 and 5 MHz, with one acting as an enhancer (e.g., boost the 2.25 MHz desired signal) and the other as a nuller (e.g., cut the 5 MHz unwanted signal).

Another example of using both filters simultaneously is to eliminate noise spikes. Here, one filter (e.g., Channel A) could be used to optimize the desired signal by dialing in its frequency and bandwidth and applying, say, +15 dB boost to create an optimal bandpass filter; the other filter (e.g., Channel B) can be tuned to null the noise spikes by sweeping through the frequency and bandwidth bands to "lock onto" the noise and applying a −15 dB cut to this band. It now may be possible to lower the flaw detector's gain, further reducing the noise level. The present version of the NSII is intended for transducers in the 1.5–7 MHz range. Transducers with up to 10 MHz center frequencies can most likely also be used since the response in a material is often much lower and falls into the NSII's operating range. Higher and lower frequency units can be made.

The following merely exemplifies, but is not limited to, specifications of the system:

Overall System Frequency Range: Two broadband filters always active to limit the output signal to the 1.5 to 7 MHz range;

By-Pass Mode: Selecting the "By-Pass" position completely removes the NSII from the circuitry; the signal can pass through to the Flaw Detector's screen with the unit either ON or OFF;

Selecting the ON setting for either "Filter" position causes the input signal to pass through the circuitry;

PreAmp: 30 dB total unfiltered gain in 10 dB steps (0, 10, 20 and 30 dB).

Tunable Bandpass Filters (identical specs for Channels A and B): Operating Mode: ON or OFF Frequency: continuously tunable from 1.5 to 7 MHz Bandwidth: three steps at approximately ±0.1 MHz (Low), ±0.5 MHz (Mid), ±1 MHz (Wide)

Filtered Gain: two steps at +15 dB (Gain) and −20 dB (Null);

Power: Source: one 9 v battery or AC/DC wall converter

Battery Duration: approx. 4–12 hours depending on the number of functions being used; and

Technique for Determining the Optimum Filter Band (for each of the independent filter channels):

1. Turn the Filter ON and set the Gain knob to the Null (−20 dB) position;

2. Sweep the Frequency knob across its band and watch for the desired signal to decrease; manipulate the frequency knob until the signal is minimized to find the signal's center frequency;

3. Sweep the Bandwidth knob across its band until the signal level further drops to a minimal level;

4. With the optimal filter band so selected, either boost (up to +15 db) or cut (down to −20 dB) the signal.

Signal Flow

IN

Low-Pass Filter (f < 7 MHz) (always On)

High-Pass Filter (f > 1.5 MHz) (always On)

PreAmp (On/Off)

Channel B Filter (On/Off)

Channel A Filter (On/Off)

OUT

Unique features of the new NSII system include:
Add-on module to any UT NDI/E instrument and independent of the UT instrument
Operates in all three NDI/E inspection modes: pulse-echo, pitch-catch and through-transmission;
Operates on single signals in real-time;
Three independent and user-settable functions for noise suppression and/or signal enhancement;
First device to use the well-known State Variable Filter (SVF) design in a novel application—UT NDI/E—and in the ultrasonic NDI/E frequency band;
First device to use narrow band variable (i.e., tunable) filters for UT applications;
Ability to tune the filter band in center frequency and width to place the optimal band over the signal of interest;
Capability of simultaneously suppressing noise and enhancing a signal of interest;
Ability to "double up" either the noise suppression or signal enhancement functions by using both filters with identical control settings;
Use of the preamp function solely as a stand-alone pre amplifier or to boost weak signals prior to the filtering operations;
Small enclosure in a hand-held package; and
Powered by either a 9 v battery or ac adapter.

In other preferred embodiments of the invention is identical in function and uses the same printed circuit board (pcb). The only difference is the frequency covered.

By changing the filters, the new NSII-L covers 0.5 to 2.4 Mhz. "L" stands for "Low" frequency. The new NSII-XL covers 0.15 to 0.7 Mhz. "XL" stands for "Extra Low" frequency.

In a further embodiment NSII-H has the same functions as the above three models, but the circuit, and hence the pcb, is different. The frequency range for the model NSII-H is 8 to 25 Mhz. "H" stands for "High" frequency.

That range is able to be changed. The range could be slightly enlarged at both the low and high ends. Changing range only involves changes of filters components on the pcb (as in the -L and -XL models), but the circuit does not change.

The two lower frequency models, NSII-L and NSII-XL, require no circuit layout changes. The circuit topology is exactly the same. Only a few component values change (i.e., resistors and capacitors) in the two filter sections to lower the frequency range to the desired respective level.

These and further and other objects and features of the invention are apparent in the disclosure, which includes the above and ongoing written specification, and the drawings.

DETAILED DESCRIPTION OF PREFERRED EMBODIMENTS

Figures 1A, 1B, 2:
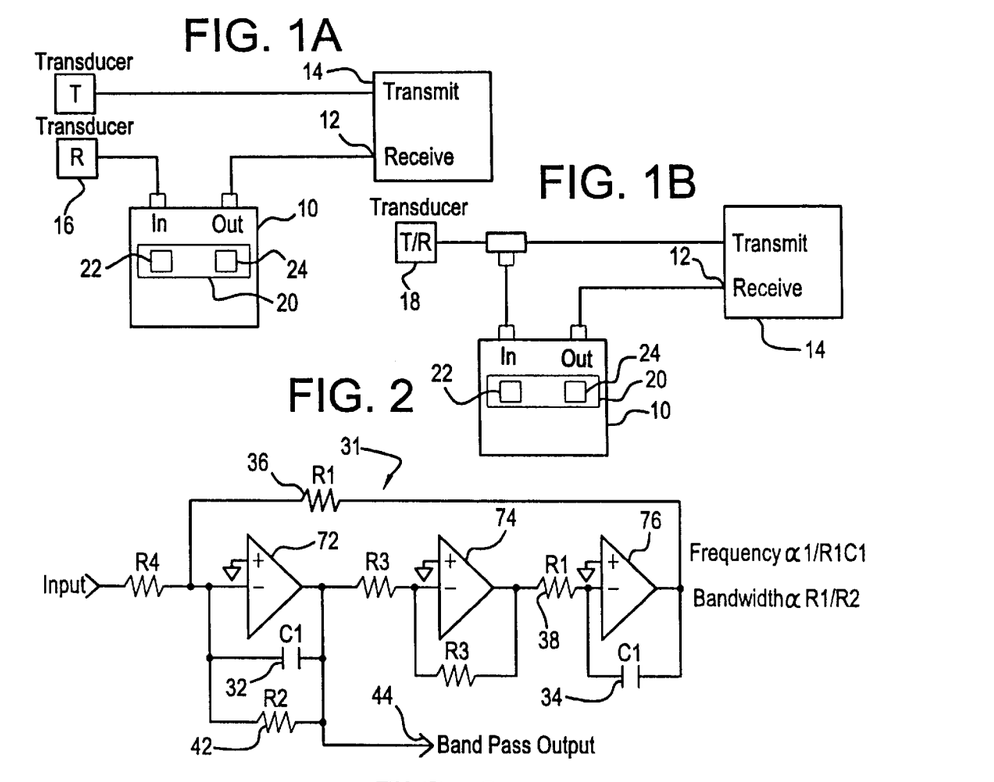
FIGS. 1a and 1b show procedures for using the NSII as an add-on unit to UT instruments in either pulse-echo or pitch-catch/through-transmission inspection modes.
FIG. 2 shows the structure of the basic state variable filter used in this invention.

The NSII system is used in conjunction with the user's UT instrument as an add-on module. As shown in FIGS. 1a and 1b, the new noise suppressor system 10 is situated between receive terminal 12 of the receive or transmit/receive user's UT instrument 14 and transducer(s) 16, 18 and contains a set of controls 20 that permits the user to sweep a wide portion of the UT NDI/E frequency band commonly used for flaw detection applications (1.5 MHz to 7 MHz) for the purpose of finding the band in which either the undesired noise or the desired signal is located.

If the user wishes to suppress the noise signal, the appropriate control is set to NULL 22, and a large decrease (−20 dB) in signal level occurs in this band. If the user wishes to enhance the desired signal, on the other hand, the appropriate control is set to GAIN 24, and a large increase (+15 dB) in signal level occurs in this band.

Filter Topology

In the new NSII unit the center frequency, bandwidth, gain of the main filter 30 elements and the state variable filter 31 shown in FIG. 2 are independently adjustable and also maintain a constant gain at the center frequency. In most forms of tuned circuits this is not possible because the components that select frequency, bandwidth and gain are the same. The second order state-variable filter 30 may be configured in such a way to allow independent control of frequency and bandwidth.

The filter circuit includes three sections: an inverting amplifier and a pair of low pass filters. The two low pass filters are tuned to the same frequency by using resistors R1 and capacitors C1 of equal value. The three sections are combined in a feedback circuit which results in a band pass function at the output of the first sections. The first section, one of the low pass filters, may have an additional resistor R2 which helps control the overall bandwidth of the filter. In this circuit the frequency is controlled by the product of R1 and C1, while the bandwidth is controlled by the ratio of R1 to R2. If R1 is held constant while varying C1 and R2, frequency and bandwidth can be independently controlled. The exact value of R3 makes no difference to the circuit, and the value of R4 only affects the overall gain of the circuit but does not affect either frequency or bandwidth.

A pair of capacitors 32, 34 are varied to provide tuning over a large range. The frequency is determined by the product of the value of these capacitors 32, 34 with two resistors 36, 38. In this circuit the value R1 of both resistors 36, 38 and capacitance C1 of both capacitors 32, 34 are identical. The bandwidth of the circuit is determined by a resistor ratio between resistor 36 at value R1 and another single resistor 42 of a different value R2. Thus if C1 is varied to control frequency and R2 is varied to control bandwidth, the two parameters are independently controllable.

Figure 4:
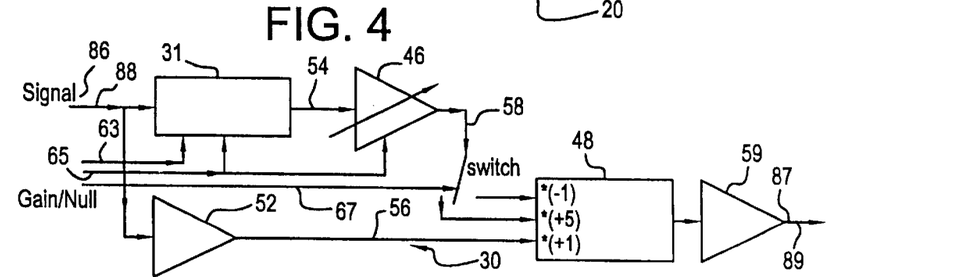
FIG. 4 shows the structure of each of the two adjustable (i.e. tunable) filters.

One problem that had to be overcome was that the gain of the filter varied with the bandwidth adjustment. As stated earlier the gain of the output 44 is supposed to be an independent parameter of the filter 30. By following the state variable filter 31 with a matched variable gain amplifier 46, as shown in FIG. 4, the output level at the center frequency of the filter/amplifier combination may be made constant over the range of bandwidth adjustments.

It was stated above that it is desirable to either enhance or remove the frequency of interest. It may also be desirable when enhancing the signal to still pass some of the "out of band" energy. To provide these functions the filter 31 output 54 is then amplified 46. The resultant signal 58 is either summed with or subtracted from the signal 56, which results from the incoming signal 86 or 88, being buffered in an amplifier 52. The summing or subtracting occurs in summing node 48. Since the output 54 of the filter 31 and the incoming signal 86 or 88 are the same level, a simple subtraction removes all energy at the selected frequency while passing unchanged any energy outside of the band of the filter. To provide the enhancement, the filtered signal 54, which is amplified 46 to signal 58, may be added to the buffered signal 56. If the filter output and incoming signal were equal, this would only provide 6 dB of enhancement, so the circuit amplifier 46 provides gain to the filter output 54 before adding the amplified filter output 58 to buffered signal 56 from the incoming signal 86 or 88. The enhancement is then adjustable and is typically set to the 10–20 dB range.

The filter output is selected by the Gain/Null control 67 to go to a port that either multiplies it by −1, for "null", or +5, for "gain" prior to summing. If −1 is selected, the output of the filter at the selected frequency and the buffered signal are the same level but opposite, and a subtraction occurs removing all energy at the selected frequency while passing unchanged any energy outside of the band of the filter. If +5 is selected, at the selected frequency the output will be 6 times the input level, providing a 16 dB enhancement. Again, any signal outside the band of interest will only be at a level of +1 provided by the buffered input.

Figure 3:
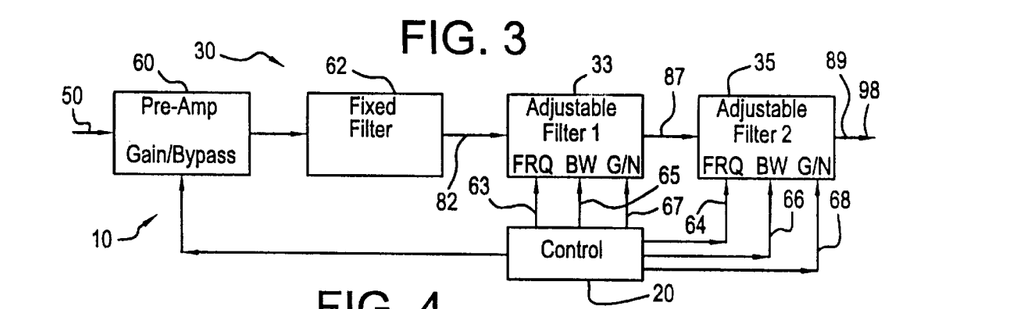
FIG. 3 presents the overall block diagram of the NSII and shows the topology of the pre-amplifier, fixed filter, dual variable filters and their associated control unit.

As shown in FIG. 3, each of the two identical tunable filters 30 may be used for either noise suppression or signal enhancement functions. Since the two filters 33, 35 operate independently, one may be set of suppress a noise signal while the other is set to enhance a signal of interest, thereby providing simultaneous noise suppression and signal/noise enhancement. Another mode of operation is where both filters are set to perform the same function—either suppress or enhance a signal—and, thereby, provide a doubling effect. This means that twice the attenuation (2×−20 dB) may be used to suppress the noise signal or twice the gain (2×+15 dB=+30 dB) may be used to enhance the desired signal.

Pre-Amplifier

Due to the nature of the filter and summing node, a great deal of noise is generated by the filter itself. This noise is equivalent to a noise source at the input of the filter. A very weak signal may be masked by this inherent noise even inside the band of interest. The large inherent noise is primarily due to having several amplifiers in the filter circuit, each with its own noise baseline level. Also, since there are several amplifiers in each filter bank, they need to have low power consumption for the device to be battery operated. Unfortunately the lowest noise amplifiers require larger amounts of power.

As shown in FIG. 3, to overcome this problem the new NSII 10 contains a pre-amplifier 60 to boost very weak signals 50 before sending them to the filters 30. The inherent noise, or noise figure, of the filter 30 is typically 10 dB more than that of a good low noise amplifier. Therefore the low noise pre-amplifier 60 provides at least 10 dB or typically 20 dB of gain before the filter 30 to allow the weak signals to overcome the filter's inherent noise. Only one of the low noise amplifiers is required to perform this function and therefore it does not severely impact power consumption. The pre-amplifier 60 may be removed from the signal path for cases where the incoming signal noise is already larger than the filter noise. In cases with large amplitude signals the additional amplification prior to the filter may cause distortion due to over-ranging of the amplifiers in the filters.

Wide-Band Filter

In ultrasonic testing the transducers resonate and therefore set up a frequency band of interest. Any energy outside of this band of interest is noise and should be removed prior to display. As shown in FIG. 3, the NSII also contains one relatively wide bandwidth, five-pole fixed filter 62 that helps eliminate any noise that is not within the band of interest. This filter 62 is made wide enough to cover the commonly used NDI/E inspection frequency range (1.5 MHz to 7 MHz). Filter 62 therefore may not be used for signal enhancement. Filter 62 is used to reduce the amplitude of large signals that are far outside the band of interest before they cause saturation of the amplifiers in the filter circuit. Saturation of the amplifiers may lead to spurious signals that appear to be in band. The fixed filter 62 works with all four units.

Control

There are three parameters of the filter circuit 30 that need to be controlled: (1) frequency, which is controlled 63, 64 by changing the value of two capacitors (32, 34 FIG. 2), (2) bandwidth, that requires the adjustment 65, 66 of a resistor 42 value R2 and the gain of an amplifier 46, and (3) the adjustments 67, 68 of overall gain or loss to be provided at the frequency of the filter. Amplifier gains and resistor values may be supplied by potentiometers. Variable capacitors 32, 34 for frequency adjustment may also be used. Variable capacitors in the required range are quite bulky and are thus not preferred in this portable instrument. Also there are cases where it is desirable to control the parameters from an outside source. In that case even potentiometers cannot be used.

To provide for external control, the first step was to replace the variable capacitors with varactor diodes 72, 74, 76. A varactor diode provides a varying capacitance given a variable DC voltage across the diode. Providing a variable voltage 63, 64 from the outside can therefore control the frequency of the filter 30. Replacing the potentiometers is more difficult, but fortunately it is not required to have a continuous range of adjustment for bandwidth and gain. It has been determined that only two or three settings 65, 66 for bandwidth, and a single selection 67, 68 of Gain or Null, are all that is required to provide good results. That allows the use of relays or solid-state switches to select between a few fixed resistors.

Figure 5:
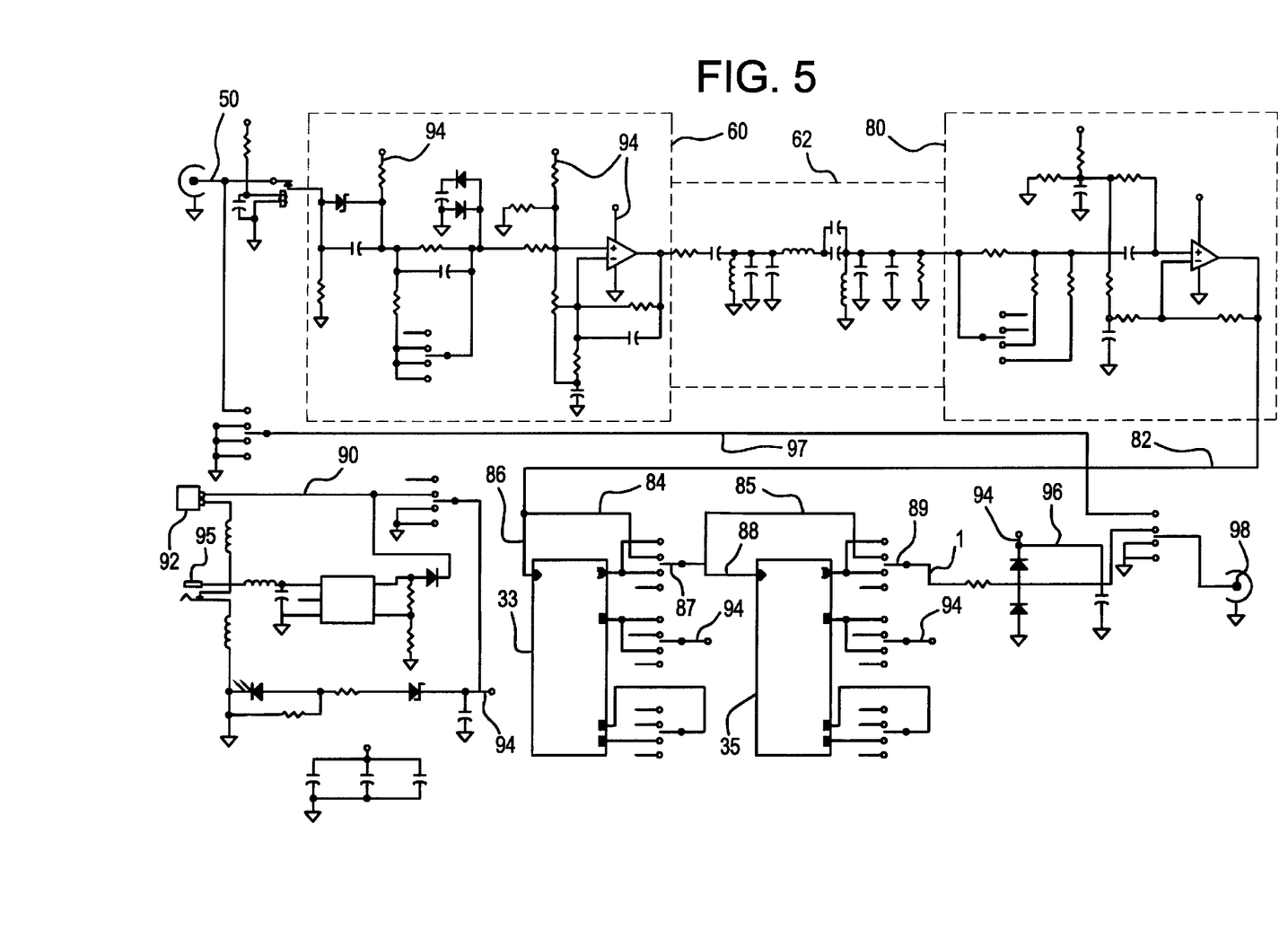
FIG. 5 shows a circuit for a noise suppressor, such as shown in FIG. 3.

FIG. 5 shows a pre-amplifier 60, an overall band pass filter 62, and a second stage pre-amplifier 80. An output 82 is provided to the first and second adjustable filters 33, 35. Bypasses 84, 85 selectively bypass inputs 86, 88 to the adjustable filter sections 33, 35. Filters 33 and 35 have outputs 87 and 89. The output 98 is provided through reverse connection protector circuit 96.

A constant voltage circuit 90 controls output 94 from an external source. When an external source is disconnected, microswitch J3 95 connects its terminals 1 and 3 to supply VBAT 94 from a battery 92. The output 94 supplies voltage to the preamps 60 and 80, to the adjustable filters 33 and 35 and to the level control 96.

In FIG. 5, switch SW1 terminal S1A controls amplification of pre-amplifier 80, and terminal S1B controls amplification of pre-amplifier. 60. Switch SW2 terminal S2B turns the battery circuit 90 on and off, and terminals S2A and S2C connect and disconnect bypass 97. Switch S3 terminals S3A controls tunable filter 33 bypass 87, S3B supplies power 94, and S3C controls null or gain of adjustable filter 33. Switch S4 terminals S4A, S4B and identical S4C control those same functions in adjustable filter 35.

Figure 6:
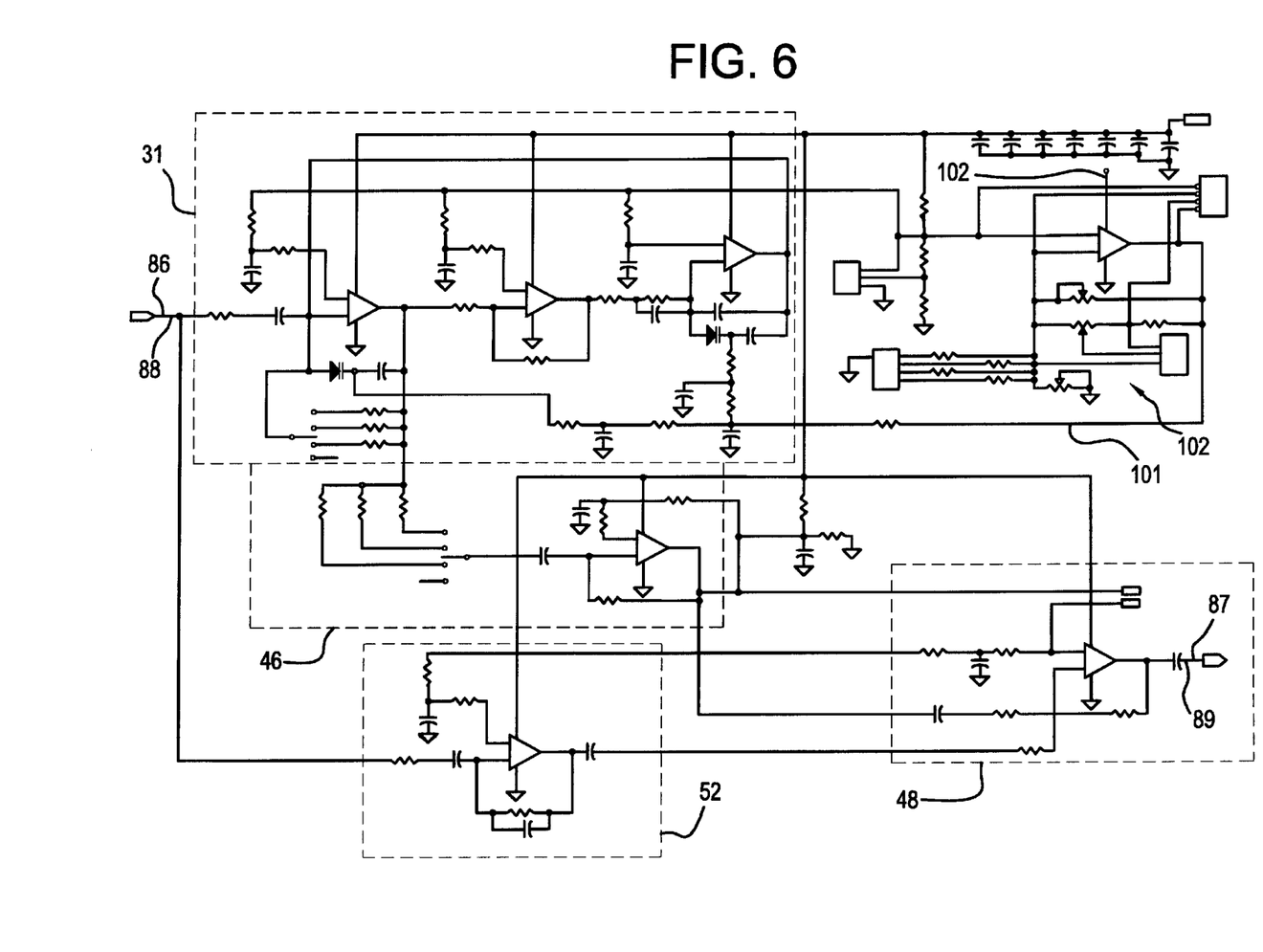
FIG. 6 shows a circuit for an adjustable filter, such as shown in FIG. 4.

In FIG. 6, tunable filters 33 and 35 from FIG. 5 are represented as filter 31. Input 86 or 88 is provided to state variable filter 31 and input buffer 2. Tuning voltage 101 is provided by tuning controller 102 to filter 31. The output of filter 31 is adjusted by bandwidth gain compensating variable amplifier 46.

In FIG. 6, switch S1 controls the tuning voltage. Switch S2 terminal S2A controls bandwidth in filter 31, and S2A controls bandwidth in the compensation amplifier 46. Null switches NULSW1 and NULSW2 control the summing node 48 to produce the output 87 or 89.

Figure 7:
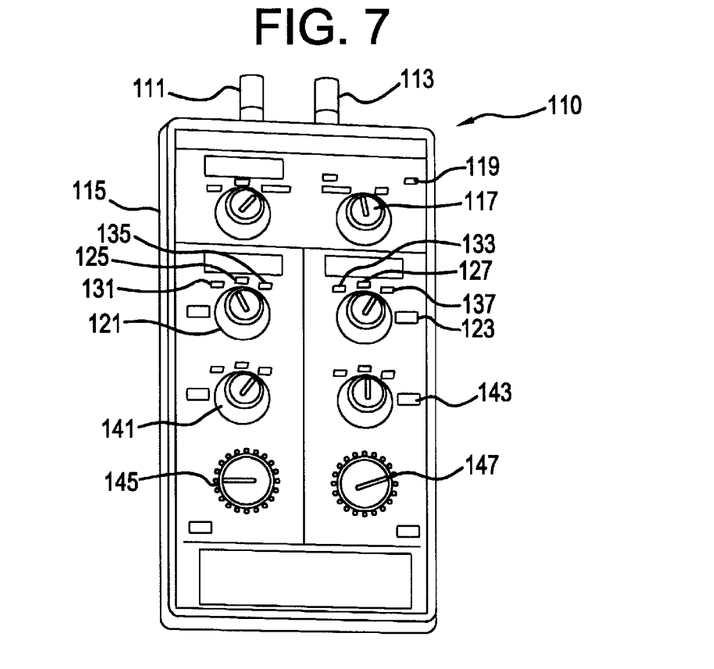
FIG. 7 shows a plug-in unit of the invention.

The noise suppressor unit 110 shown in FIG. 7 has input and output connectors 111 and 113. The impedance range is at input 150 ohms and at output 50 ohms. Switch 115 controls terminals S1A and S1B in FIG. 5 and selects the pre-amplifier range, from 0 to 30+dB.

Switch 117 in FIG. 7 controls terminals S2A, S2B and S2C in FIG. 5 and bypasses the unit and allows before and after filtering comparisons. A power indicator is a red LED 119 which functions as an on/off indicator. The source is a 9 volt battery or AC connection. For a low battery, the display 119 turns off when output drops below 7 volts.

Switches 121 and 123 are the null or gain controls (S3 and S4 in FIG. 5) for filters 33 and 35. The filters are two independent manually tunable filters, and have the null-gain controls for ON/OFF positioning. For noise suppression, Null settings 131, 133 give −20 dB attenuation; for signal enhancement, Gain settings 135, 137 give +15 dB.

Bandwidth controls 141, 143 (switch S2 in FIG. 6) provide low (bw=20% of center frequency), mid (bw=30% of center frequency), and wide (bw=60% of center frequency) settings.

Frequency controls 145, 147 provide range of 1.5 to 7 MHz, with 16 steps. Step sizes are 0.25 MHz (1.5–3 MHz), 0.33 MHz (3–4 MHz), and 0.50 MHz (4–7 MHz).

The noise suppressors unit 110 have rugged construction. The switches are detented rotary switches. The enclosure is 94HP plastic with nickel-based EMI/RFI shielding. The dimensions are 7" L×4" W×1.5" D (17.8 cm×10.2 cm×3.8 cm). The weight is 14 ounces (0.397 kg).

The new Noise Suppressor II™ is easy to set up and use. Portable (7"×4"×1.5"; 14 oz.) and rugged. It is perfect for field use. It is placed between transducer(s) and a UT instrument and operates in both pulse-echo and pitch-catch/thru-transmission modes. The new noise suppressor is battery or AC powered and gives significant performance boost to old or new, analog or digital UT instruments.

The NSII is connected between the transducer(s) and the pulser/receiver or flaw detector. It is housed in a small (7"×4"×1.5") enclosure weighing 14 ounces and is powered by either a 9 v battery or AC. It operates in both pulse-echo and pitch-catch/thru-transmission modes. All settings are via detented rotary switches so that the user is assured of repeatable inspections. The unit interfaces with any type of analog instrument for repeatable inspections. The unit interfaces with any type of analog or digital ultrasonic unit to provide an add-on enhancement. Typical responses of the unit are shown in the before and after graphical representations in FIGS. 8A–D.

Figure 8A:
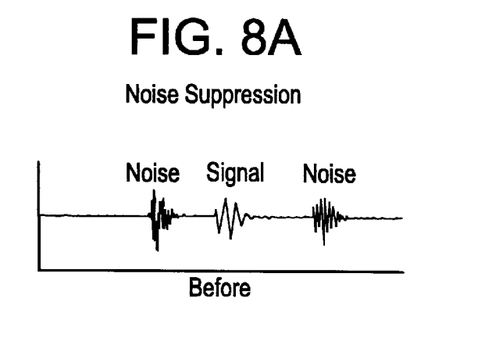
FIGS. 8A–D show typical signal noise suppressed and enhanced wave forms.
Figure 8B:
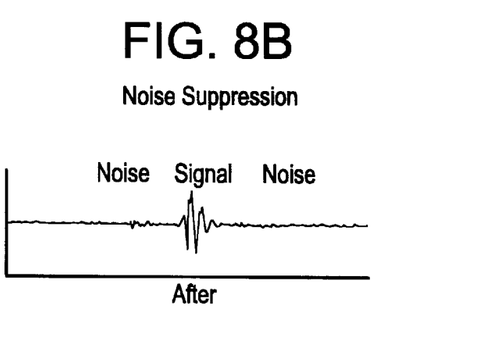
Figure 8C:
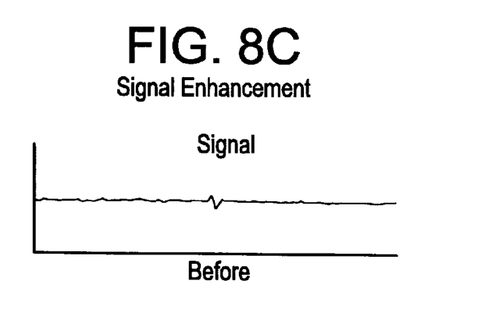
Figure 8D:
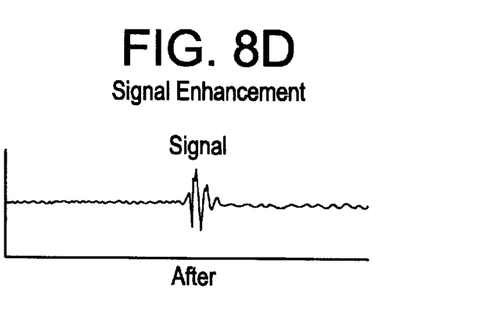

When a signal is strong, both filters A and B as shown in FIG. 8A may be adjusted for noise suppression with a result as shown in FIG. 8B. When a signal is weak, as shown in FIG. 8C, both filters may be adjusted for signal enhancement with the result as shown in FIG. 8D.

In one embodiment there are three models (i.e., versions) of the Noise Suppressor II. They are identical in function and use the same printed circuit board (pcb). The only difference is the frequency range each covers. This is implemented by a change of only a few components on the pcb's (i.e., some resistor and capacitor values). No change in the pcb itself was needed. The 3 models and their respective frequency ranges are:

NSII—1.5 to 7 MHz

NSII-L—0.5 to 2.4 MHz ("L" stands for "Low" frequency)

NSII-XL—0.15 to 0.7 MHz ("XL" stands for "Extra Low" frequency)

A 4$^{th}$ model, NSII-H ("H" stands for "High" frequency) has the same functions as the above 3 models, but the circuit, and hence the pcb, is different. The frequency range for the model NSII-H is 8 to 25 MHz.

That range is able to be changed. The range could be slightly higher at both the low and high ends. Changing range only involves changes of components on the pcb (as in the -L and -XL models), but the circuit does not change.

The two lower frequency models, NSII-L and NSII-XL, require no circuit layout changes. The circuit topology is exactly the same. Only a few component values change (i.e., resistors and capacitors) in the two filter sections to lower the frequency range to the desired respective level.

These are simple extensions to the NSII technology, and no further diagrams are needed.

On the other hand, a high frequency model, NSII-H, has a major circuit layout change. The ON/OFF-BYPASS and preamp sections are the same, but the filter topology is completely different. This is due to the filters, themselves, being completely different. The NSII and the NSII-L and NSII-XL are implemented as "state variable filters". The state variable filter is, in essence, a Gaussian distribution (i.e., very peaked) and the width (and, hence, roll-off) of the filter is controlled by the bandwidth (BW) switch with three positions—Low, Mid, High—which acts like the standard deviation of the distribution. A BW switch in the LOW position creates a very peaked distribution; a BW in the HIGH position creates a less peaked, broader distribution.

The NSII-H, on the other hand, implements the filters using passive circuitry to simply design at higher frequencies. Another change is that there is only one filter assembly, rather than two, for the NSII-H. The filter is tunable over the range of 8 to 25 MHz, in six discrete steps of 8, 10, 12, 15, 20, and 25 MHz.

As with the NSII and its low frequency modifications—NSII-L and NSII-XL—that were implemented by simple component substitutions to an existing circuit layout, and NSII-H, too, is able to have modifications, also be simple substitutions to the existing circuit layout.

Figure 9:
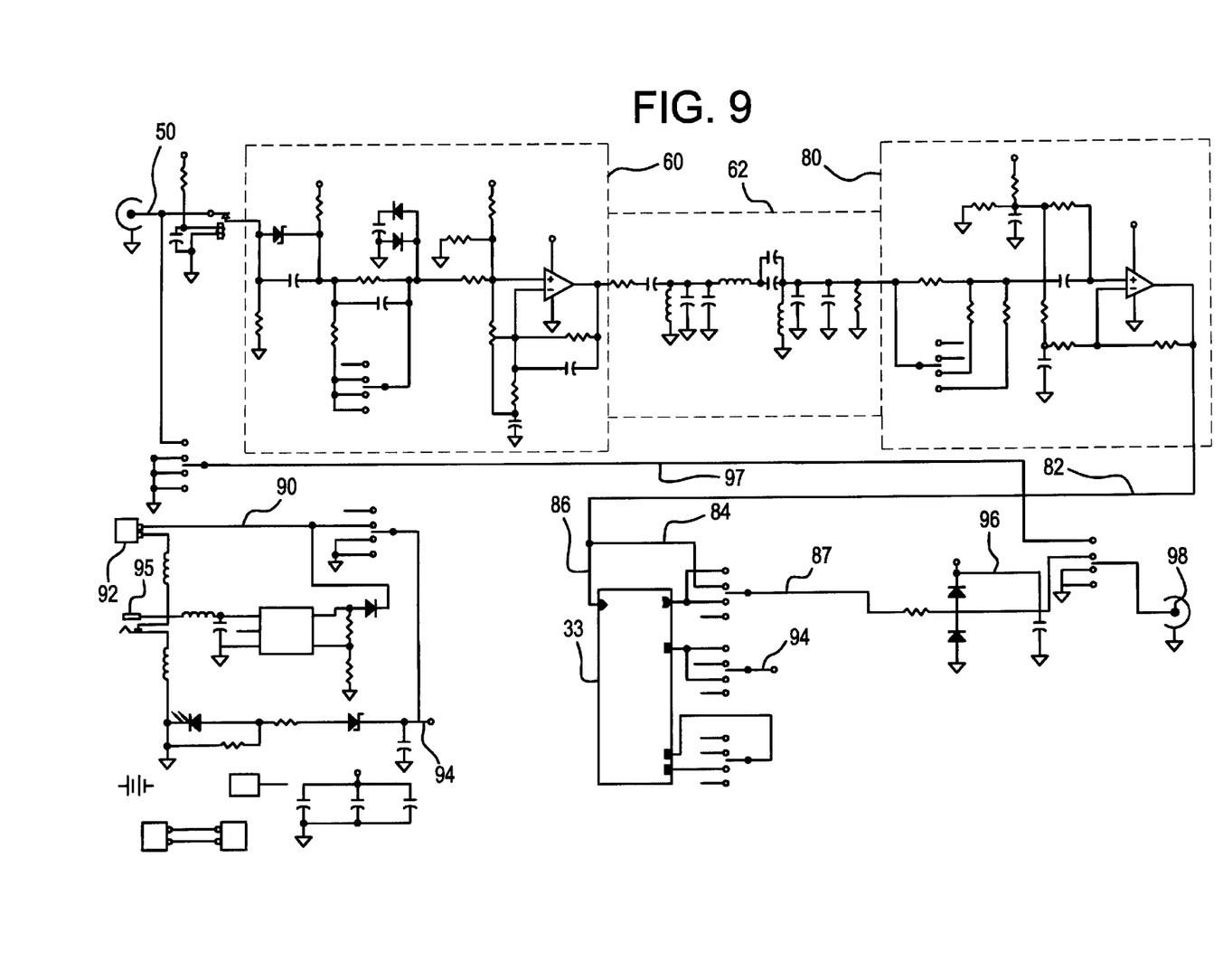
FIG. 9 is a schematic diagram of an ultrasonic noise suppression inspection using a single bank of filters.
Figure 10:
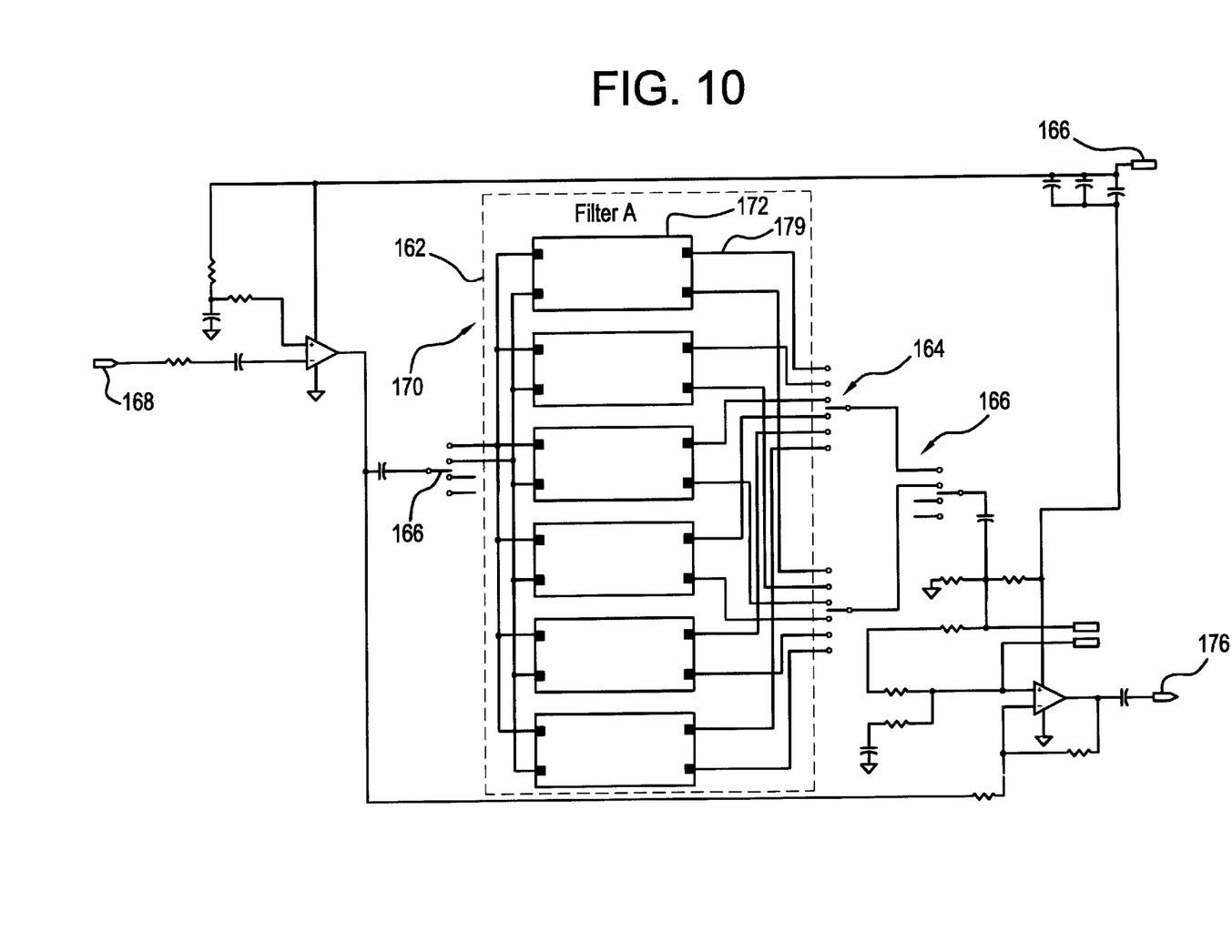
FIG. 10 is a schematic representation of the bank of filters and the switch is for selecting individual filters within the bank of filters as used in FIG. 7.

FIGS. 9–10 show the "-H" version of the NSII. There are similarities between new FIGS. 9–11 and FIGS. 1–6 in the application.

FIG. 9, with three blocks identified as (PreAmp Stage 1, Overall Band Pass Filter and PreAmp Stage 2,) is similar to FIG. 5.

FIG. 10 shows a band or assembly of single filters which may be selected individually.

Figure 11:
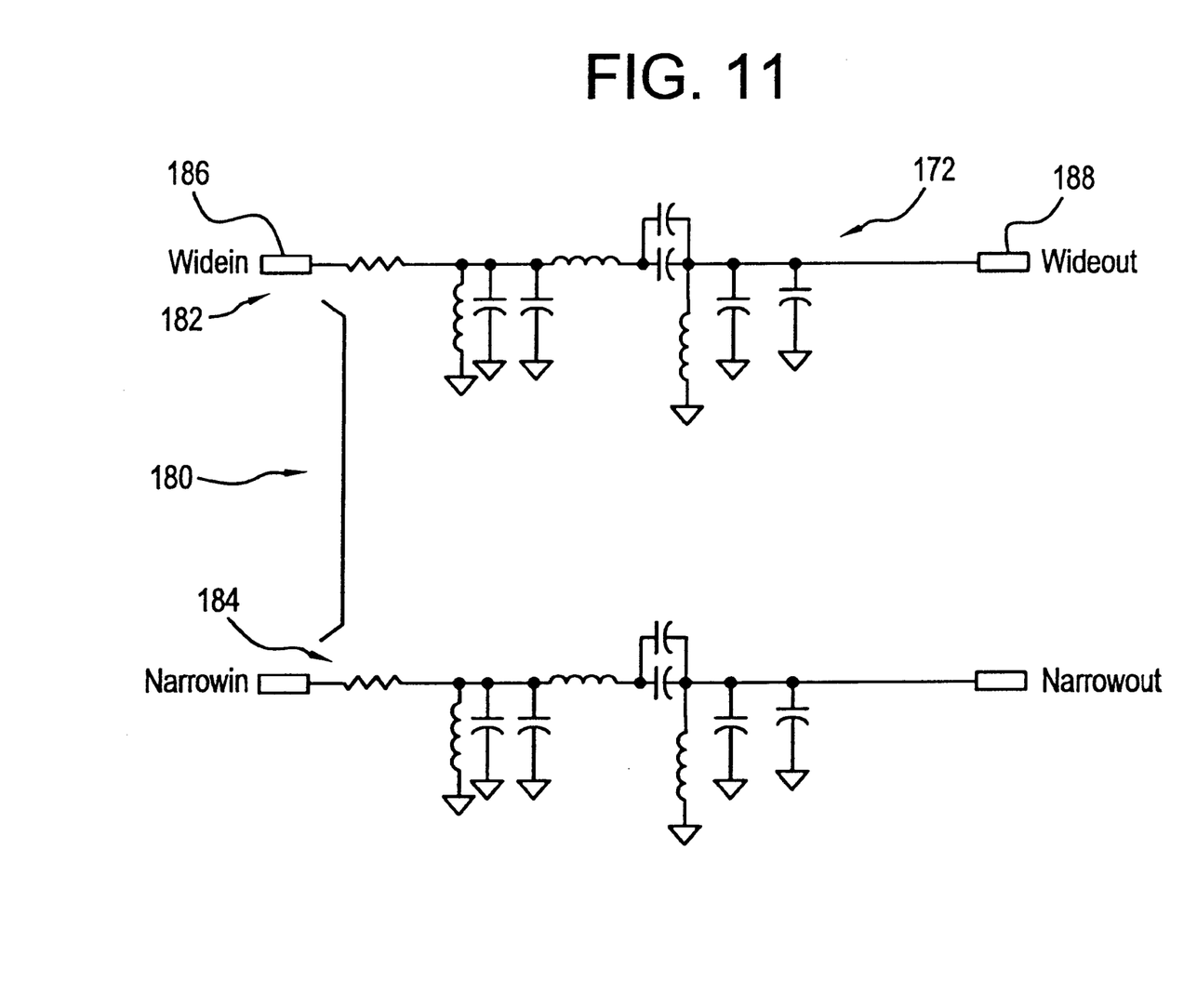
FIG. 11 shows components of an individual filter within the bank of filters shown in FIG. 10.

FIG. 11 shows components of one filter in the bank of filters shown in FIG. 10.

There are two major difference between the new "-H" version 150 shown in FIGS. 9–11 and the "regular" NSII version (which covers the NSII, NSII-L and NSII-XL models), as already described.

The NSII-H has only one Filter 160 for the entire frequency range, rather than the two Filters in the NSII, each performing identical functions.

The NSII-H uses a bank 162 of fixed filters, each with its own frequency and bandwidths, rather than one, tunable filter as in the NSII. The NSII-H has 6 discrete frequencies (8, 10, 12, 15, 20 and 25 MHz), selected by switch 164, and each has two bandwidth choices (narrow or wide) selected by switch 166 for each frequency. The "-H" model has a separate subcircuit for each of the 12 choices (6 frequencies×2 bandwidth per frequency) as shown in FIGS. 10 and 11. In contrast, the NSII has only one filter circuit, and performance is "tunable" over the frequency range. The six frequencies values can easily be changed by component changes; FIG. 11 shows one of the six filter banks that are shown in FIG. 10. They are all identical, so only one is shown, notwithstanding that all six exist within one instrument.

As shown in FIG. 10 DC power 166 is conditioned and supplied to amplifiers U8 and U11. Signal input 168 is supplied to amplifier U8, and the amplified signal 170 is supplied via bandwidth switch 166 to either wide or narrow inputs of all filters 172 in the filter bank switch 166 through which terminal S7C selects either wide or narrow inputs and outputs of all filters 172 and to output amplifier U11.

Switch 164 through terminal S2A selects one of the outputs 179 in a frequency range from one of the preset filters 172 in filter bank 162. The selected output is conditioned and provided to the output operational amplifier U11, which provides a noise suppressed and amplified signal output on terminal 176.

In FIG. 11 a typical one of the filters 172 in filter bank 162 has channels 180. The separate channels 180 include a wide band channel 182 and a narrow band channel 184. Electronic components are arranged in each channel in similar structure with different values of resistance, capacitance and impedance. The same structure with different values is used in each filter 172 in the bank 162 to target narrow or wide bands in specified frequency ranges. The inputs 186 are selected by switch 166 which selects the bands, as shown in FIG. 10. The outputs 188 are selected by switch 164, which selects the particular filter 172 in bank 162.

The fixed filter and pre-amplifier circuits remain essentially unchanged when extending the design to higher frequencies about 7 MHZ. The state variable filter circuitry needs to be modified. Available analog components have less gain at these higher frequencies, and this causes a decrease in the filter's response. Also, stray capacitance can lead to oscillations and difficulty compensating the filter's output level. Because of these high-frequency issues, the filter circuitry design implements a group, or "bank", of passive filters, rather than a single, tunable filter. Each passive filter, in the modified design, is tuned for a specific frequency and bandwidth. The frequency switch now is used to select between the various filters 172 in the bank 162 of fixed-tuned filters. This method is less flexible than the single tunable approach because it does not provide for a virtually continuously variable frequency, but it does provide enough frequency choices so that the high frequency model is still a useful instrument in the ultrasonic flaw detector market. For the modified design, a total of six frequencies and two bandwidths are supported by a bank of twelve filters, with each filter representing one of the 6×2= 12 choices of frequency and bandwidth. This approach, which is highly stable and does not suffer from oscillations or low output levels, requires more circuit board areas for implementation. Because this design is much less efficient on space, only one filter section is available as opposed to two when using state variable filters at the lower frequencies. Additionally, the choice of the specific values for the six frequencies can be changed by simply a change of components. Initially, the six frequency values were set at 8, 10, 12, 15, 20 and 25 MHz, but another choice, such as 8, 10, 15, 20, 25 and 30 MHz, can be created at any time by appropriate component changes.

The invention provides noise suppression and signal enhancing for an ultrasonic non-destructive inspection apparatus. An ultrasonic source has a transducer connected to the source and positioned on an article being inspected or evaluated. One or more transducers are positioned on the article being evaluated. An input of a noise suppressor and signal enhancer is connected to the transducer(s). A first preamplifier is connected to the input. An overall bypass filter is connected to the first preamplifier. A second variable preamplifier is connected to the overall band pass filter. A filter assembly is connected to the variable preamplifier. The filter assembly has an output for connecting the apparatus to a signal analyzer.

While the invention has been described with reference to specific embodiments, modifications and variations of the invention may be constructed without departing from the scope of the invention.

We claim:

1. Noise suppressing, signal enhancing, ultrasonic nondestructive inspection apparatus comprising an ultrasonic signal source and a return signal analyzer, a transducer connected to the source and positioned on an article being inspected, one or more receiving transducers positioned on the article being inspected, a noise suppressor and amplifier unit having an input connected to the receiving transducers, a first pre-amplifier stage connected to the input, a fixed filter connected to the first pre-amplifier, a second, adjustable pre-amplifier stage connected to the fixed filter, a filter assembly having an input connected to the second pre-amplifier stage, the filter assembly having an output for connecting to the return signal analyzer.

2. The apparatus of claim 1, wherein the filter assembly comprises first and second series-connected tunable filters.

3. The apparatus of claim 2, wherein each of the tunable filters comprises a state variable filter, a bandwidth gain compensation circuit connected to an output of the state variable filter and a summing node connected to an output of the band compensation circuit.

4. The apparatus of claim 3, further comprising a bandwidth selection switch for selecting wide, middle or narrow bandwidths, connected to each of the state variable filters and to each gain compensation circuit.

5. The apparatus of claim 2, wherein each tunable filter has connected thereto a frequency selector for selecting a center frequency and an amplification selector for selecting positive, negative or no amplification.

6. The apparatus of claim 1, wherein the second preamplification stage further comprises a variable amplifier.

7. The apparatus of claim 1, wherein the filter assembly comprises an array of tuned filters and a switch severally connected to the filters for selecting output of one of the tuned filters.

8. The apparatus of claim 7, wherein each of the tuned filters has a wide band filter and a narrow band filter and further comprising a band selector switch connected to the wide band filter and to the narrow band filter in each of the tuned filters for selecting either wide or narrow band filters.

9. Module apparatus for use in an ultrasonic inspection system comprising a housing having a module input and a module output mounted thereon, a pre-amplifier connected to the module input, a fixed bandwidth filter connected to the pre-amplifier, an adjustable filter assembly having an input connected to an output of the pre-amplifier and having an output connected to the module output and switches connected to the filter assembly for selecting bandwidths and center frequencies of the filter assembly.

10. The apparatus of claim 9, wherein the filter assembly comprises a first adjustable filter having an input connected to an output of the pre-amplifier, a second adjustable filter having an input connected to the first adjustable filter and having an output connected to the module output.

11. The apparatus of claim 10, further comprising a bypass for connecting the module input to the module output, a bypass switch for closing and opening the bypass, and frequency, bandwidth, suppressor and amplifier controls connected to the first and second adjustable filters for independently selecting center frequencies, wide, mid or narrow bandwidths and null or gain of the first and second adjustable filters respectively.

12. The apparatus of claim 10, wherein the adjustable filters further comprise variable amplifiers and further comprise controls connected to the variable amplifiers for connecting levels of power to the variable amplifiers for providing negative (null) or positive amplification in the adjustable filters.

13. The apparatus of claim 10, further comprising a second pre-amplifier having a variable amplifier connected between the fixed filter and the first adjustable filter.

14. The apparatus of claim 13, further comprising amplifier controls connected to the variable amplifier in the second pre-amplifier for changing dB output of the second pre-amplifier.

15. The apparatus of claim 9, further comprising a second pre-amplifier stage having selectable pre-amplification connected to the fixed bandwidth filter, and wherein the tuned filter assembly comprises a bank of independent filters having distinct center frequencies.

16. The apparatus of claim 15, wherein each of the independent filters has a wide bandwidth channel and a narrow bandwidth channel, and further comprising a bandwidth switch connected to the independent filters for selecting the wide or narrow bandwidth channels.

17. The apparatus of claim 9, wherein the filter assembly comprises an array of tuned filters and a switch severally connected to the filters for selecting output of one of the tuned filters.

18. The apparatus of claim 17, wherein each of the tuned filters has a wide bandwidth filter and a narrow bandwidth filter and further comprising a bandwidth selector switch connected to the wide band filters and to the narrow band filters for selecting either wide or narrow bandwidth filters.

19. A noise suppressor and signal enhancement ultrasonic module apparatus for connecting between a return signal receiving transducer and a signal analyzer comprising a module, an input on the module for connecting to the receiving transducer and an output on the module for connecting to the analyzer, a first pre-amplifier stage connected to the input, a fixed bandwidth filter connected to the first pre-amplifier stage, a second, adjustable pre-amplifier stage connected to the bandwidth filter, and an assembly of filters connectable individually to the second pre-amplifier stage and connectable to the output.

20. The apparatus of claim 19, wherein the assembly of filters comprises first and second series-connected tunable filters, controls mounted in the module and connected to the tunable filters for individually selecting center frequencies of the filters, wide, narrow or middle bandwidths of the filters and nulling or amplifying of the signals in the selected bandwidths around the selected center frequencies.

21. The apparatus of claim 19, wherein the assembly of filters comprise series-connected tunable filters and wherein each of tunable filters comprises a state variable filter and a bandwidth gain compensation circuit connected to an output of the state variable filter and a summing node connected to an output of the bandwidth compensation circuit.

22. The apparatus of claim 21, further comprising a three-position narrow, wide and mid bandwidth selection switch mounted on the module and connected to each of the state variable filters and to each gain compensation circuit.

23. The apparatus of claim 20, wherein each tunable filter has a center frequency selector and an amplification selector for individually selecting nulling or amplifying of frequencies in the selected bandwidth around the selected center frequency in each of the tunable filters.

24. The apparatus of claim 19, wherein the second pre-amplification stage has selectable amplification.

25. The apparatus of claim 19, wherein the assembly of filters comprises a bank of tuned filters and a switch severally connected to the filters for selecting output of one of the tuned filters.

26. The apparatus of claim 25, wherein each of the tuned filters has a wide bandwidth filter and a narrow bandwidth filter, and further comprising a bandwidth selector switch connected severally to the wide bandwidth filter and to the narrow bandwidth filter in each of the tuned filters for selecting either wide or narrow bandwidth output as the selected output.

27. A method of selectively enhancing and suppressing return signals from one or more ultrasonic inspection transducers comprising switching the return signals between a bypass and an amplifier, pre-amplifying the signals, removing out-of-band signals, passing in-band signals to an adjustable amplifier, amplifying and controlling amplification of the in-band signals, providing a filter assembly, passing the in-band amplified signals to the filter assembly, selecting filters in the assembly, selecting bandwidths of the selected filters in the assembly, selecting center frequencies of the filters and producing an output at the selected frequency and bandwidth with signal enhancing and noise suppression.

28. The method of claim 27, further comprising selecting amplifying or nulling of the signal in the filter assembly.

29. The method of claim 27, wherein the providing a filter assembly comprises providing first and second series-connected filters wherein the selecting bandwidths comprises separately selecting narrow, wide or mid bandwidths in each of the first and second filters.

30. The method of claim 29, further comprising separately selecting the negative (nulling) amplification or positive amplification in the first and second filters.

31. The method of claim 27, wherein the providing a filter assembly comprises providing a bank of tuned filters with distinct center frequencies and providing wide bandwidth filters and narrow bandwidth filters for each center frequency, and wherein the selecting further comprises selecting wide bandwidth filters or narrow bandwidth filters and selecting one of the tuned filters from the bank of filters according to its center frequency.

* * * * *